(12) United States Patent
Thacker et al.

(10) Patent No.: US 11,123,565 B1
(45) Date of Patent: *Sep. 21, 2021

(54) TREATMENT OF NEURODEGENERATIVE DISEASE WITH HIGH FREQUENCY STIMULATION, AND ASSOCIATED SYSTEMS AND METHODS

(71) Applicant: Nevro Corp., Redwood City, CA (US)

(72) Inventors: James R. Thacker, Homer, AK (US); Kerry Bradley, Glendale, CA (US); Dongchul Lee, Agua Dulce, CA (US)

(73) Assignee: Nevro Corp., Redwood City, CA (US)

( * ) Notice: Subject to any disclaimer, the term of this patent is extended or adjusted under 35 U.S.C. 154(b) by 455 days.

This patent is subject to a terminal disclaimer.

(21) Appl. No.: 15/798,110

(22) Filed: Oct. 30, 2017

Related U.S. Application Data

(60) Provisional application No. 62/415,429, filed on Oct. 31, 2016.

(51) Int. Cl.
*A61N 1/18* (2006.01)
*A61N 1/36* (2006.01)
*A61N 1/06* (2006.01)

(52) U.S. Cl.
CPC ........... *A61N 1/36171* (2013.01); *A61N 1/06* (2013.01); *A61N 1/36062* (2017.08); *A61N 1/36082* (2013.01); *A61N 1/36175* (2013.01)

(58) Field of Classification Search
CPC .............................. A61N 1/06; A61N 1/36062
See application file for complete search history.

(56) References Cited

U.S. PATENT DOCUMENTS

| | | |
|---|---|---|
| 5,707,396 A | 1/1998 | Benabid |
| 7,313,442 B2 | 12/2007 | Velasco et al. |
| 7,346,395 B2 | 3/2008 | Lozano et al. |
| 7,653,433 B2 | 1/2010 | Lozano et al. |
| 8,190,264 B2 | 5/2012 | Lozano et al. |
| 8,195,298 B2 | 6/2012 | Lozano et al. |
| 8,280,514 B2 | 10/2012 | Lozano et al. |
| 8,315,703 B2 | 11/2012 | Lozano et al. |
| 8,355,797 B2 | 1/2013 | Caparso et al. |
| 8,428,735 B2 | 4/2013 | Littlewood |
| 8,467,878 B2 | 6/2013 | Lozano et al. |
| 8,712,533 B2 | 4/2014 | Alataris et al. |
| 8,798,754 B2 | 8/2014 | Knudson et al. |
| 8,849,392 B2 | 9/2014 | Lozano et al. |

(Continued)

FOREIGN PATENT DOCUMENTS

WO  WO-2015013252  1/2015

OTHER PUBLICATIONS

U.S. Appl. No. 15/365,846, filed Nov. 30, 2016, Lee.

(Continued)

*Primary Examiner* — Alyssa M Alter
(74) *Attorney, Agent, or Firm* — Perkin

(57) ABSTRACT

Systems and methods for treating neurodegenerative disorders with high frequency stimulation are disclosed. A representative method for treating a patient includes applying an electrical signal to the patient via a treatment system that includes a signal delivery element positioned at or within a white matter of the patient's brain, spinal cord, or both, the electrical signal having a frequency of from about 1.5 kHz to about 100 kHz.

14 Claims, 5 Drawing Sheets

(56) References Cited

U.S. PATENT DOCUMENTS

| | | | |
|---|---|---|---|
| 8,909,342 B2 | 12/2014 | Lozano et al. | |
| 9,278,215 B2 | 3/2016 | Thacker et al. | |
| 9,327,121 B2 | 5/2016 | Thacker et al. | |
| 9,446,238 B2 | 9/2016 | Lozano et al. | |
| 9,884,198 B2 | 2/2018 | Parker | |
| 9,895,539 B1 | 2/2018 | Heit et al. | |
| 10,493,275 B2 | 12/2019 | Alataris et al. | |
| 2004/0111127 A1 | 6/2004 | Gliner | |
| 2005/0197678 A1 | 9/2005 | Bojeva | |
| 2006/0004422 A1* | 1/2006 | De Ridder | A61N 1/0531 607/45 |
| 2006/0155348 A1 | 7/2006 | deCharms | |
| 2006/0161218 A1 | 7/2006 | Danilov | |
| 2009/0054829 A1 | 2/2009 | Chen | |
| 2009/0204173 A1 | 8/2009 | Fang et al. | |
| 2010/0191307 A1 | 7/2010 | Fang et al. | |
| 2010/0274312 A1 | 10/2010 | Alataris et al. | |
| 2010/0274317 A1 | 10/2010 | Parker et al. | |
| 2011/0071593 A1 | 3/2011 | Parker et al. | |
| 2012/0065699 A1 | 3/2012 | Bedenbaugh | |
| 2012/0172946 A1 | 7/2012 | Alataris et al. | |
| 2013/0066411 A1 | 3/2013 | Thacker et al. | |
| 2014/0316497 A1 | 10/2014 | Gaunt et al. | |
| 2015/0217116 A1 | 8/2015 | Parramon et al. | |
| 2016/0175594 A1 | 6/2016 | Min | |
| 2017/0165485 A1 | 6/2017 | Sullivan et al. | |
| 2017/0216587 A1 | 8/2017 | Parker | |
| 2017/0281949 A1 | 10/2017 | Thacker et al. | |
| 2018/0280691 A1 | 10/2018 | Ackermann et al. | |

OTHER PUBLICATIONS

U.S. Appl. No. 15/606,869, filed May 26, 2017, Lee.
U.S. Appl. No. 16/663,255, filed Oct. 24, 2019, Pannu.
U.S. Appl. No. 16/127,098, filed Sep. 10, 2018, Pannu.
Steigerwald et al., "Pulse Duration Settings in Subthalamic Stimulation for Parkinson's Disease," Movement Disorders, vol. 33, No. 1, 2018, 5 pages.
Dayal et al., "Subthalamic Nucleus Deep Brain Stimulation in Parkinson's Disease: The Effect of Varying Stimulation Parameters," Journal of Parkinson's Disease 7, 2017, 11 pages.
Akbari et al., "The proposed mechanisms of radio frequency waves (RFWs) on nervous system functions impairment," Comp Clin Patho, 2015, 13 pages.
Benabid et al., "Chronic electrical stimulation of the ventralis intermedius nucleus of the thalamus as a treatment of the movement disorders," Journal of Neurosurg, 1996, 12 pages.
Benabid et al., "Deep brain stimulation of the subthalamic nucleus for the treatment of Parkinson's disease," www.thelancet.com/neurology, vol. 8, Jan. 2009, 15 pages.
Benabid et al., "Long-Term suppression of tremor by chronic stimulation of the ventral intermediate," The Lancet, vol. 337, 1991, 4 pages.
Benabid et al.,"Chronic Electrical Stimulation of the Ventralis Intermedius Nucleus of the Thalamus and of Other Nuclei as a Treatment of Parkinson's Disease," Techniques in Neurosurgery, vol. 5, No. 1, 1999, 26 pages.
Cabezas et al., "The role of glial cells in Alzheimer disease: potential therapeutic implications," Neurologia, 2014, 5 pages.
Holm et al., "Insights into Pathology of the ∞3 Na+/K+-ATPase Ion Pump in Neurological Disorders; Lessons from Animal Models," Frontier in Physiology, 2016, 12 pages.
Kann, Oliver, "The interneuron energy hypothesis: Implications for brain disease," Neurobiology of Disease, 2015, 11 pages.
Kinoshita et al., "The Influence of Na+, K+-ATPase on Glutamate Signaling in Neurodegenerative Diseases and Senescence," Frontiers in Physiology, Jun. 2016, 19 pages.
Liu et al., "Activation of Na+ and K+ Pumping Modes of Na,k)-ATPase by an Oscillating Electric Field," The Journal of Biological Chemistry, vol. 265, May 5, 1990, 9 pages.
Miller et al., "Electric Field Driven Torque in ATP Synthase," PLOS One, vol. 8, Issue 9, Sep. 2013, 9 pages.
Tsong, Tian Yow, "Electrical Modulation of Membrane Proteins: Enforced Conformational Oscillations and Biological Energy and Signal Transductions," Annu. Rev. Biophys. Biophys. Chem., 1990, 24 pages.
Vitvitsky et al., "Na+ and K+ ion imbalances in Alzheimer's disease," Biochimica et Biophysica Acta, ELSEVIER, 2012, 11 pages.

* cited by examiner

TREATMENT OF NEURODEGENERATIVE DISEASE WITH HIGH FREQUENCY STIMULATION, AND ASSOCIATED SYSTEMS AND METHODS

CROSS-REFERENCE TO RELATED APPLICATION

The present application claims priority to U.S. Provisional Application No. 62/415,429, filed on Oct. 31, 2016 and incorporated herein by reference.

TECHNICAL FIELD

The present technology is directed generally to treatment of neurodegenerative disease with high frequency stimulation, and associated systems and methods.

BACKGROUND

The plasma membrane of a cell is responsible for maintaining the cell's resting membrane potential (or the voltage difference between the cell's extracellular space and intracellular space), when the cell is in a resting state (e.g., not receiving any external stimuli). For example, the average resting membrane potential for a typical neuron is about −70 mV (with the intracellular fluid more negative than the extracellular fluid) and enables the neuron to generate electrical signals. A neuron's ability to generate and propagate an electrical signal is critical to the transfer of information within the nervous system. Neuronal signaling, for example, typically occurs via the following pathway: (1) a neuron, in a resting state, receives a physical, electrical, electromagnetic, acoustic, or chemical signal at the membrane; (2) the received signal opens a particular type of positive ion (cation) channel spanning the membrane (e.g., channels specific to sodium ions), thereby allowing an influx of specific positive ions (e.g., $Na^+$, $Ca^{2+}$) into the intracellular space; (3) the influx of these particular positive ions depolarizes (makes less negative) the intracellular space at the membrane near the affected ion channel; (4) the local depolarization causes nearby voltage-gated, positive ion channels to open, thereby further depolarizing the local intracellular space; (5) once the localized depolarization reaches a membrane potential value more positive than a certain membrane potential threshold, an action potential is generated that propagates along the membrane, thereby creating an electrical current flow in the neuron. When the current reaches the neuron's axon terminal, the neuron releases neurotransmitters that bind to receptors on an adjacent neuron, thereby chemically transmitting the signal.

The magnitude of the resting membrane potential greatly affects the neuron's ability to generate an action potential, and thus greatly affects the neuron's ability to effectively communicate with other neurons. The magnitude of the resting membrane potential depends primarily on (1) differences in ion concentration between the intracellular and extracellular fluid, and (2) the cell membrane's selective permeability to different ions. Of the different ions present within the intracellular and extracellular fluid of a typical animal cell, sodium and potassium ions are present in the largest concentrations. As such, the respective concentration gradients of sodium and potassium ions across the cell membrane have a large impact on the membrane potential.

One cellular component responsible for establishing and maintaining the respective concentration gradients of sodium and potassium is an enzyme known as sodium-potassium adenosine triphosphatase or "$Na^+/K^+$-ATPase." $Na^+/K^+$-ATPase is an electrogenic transmembrane pump found in the membrane of all animal cells, and actively pumps three sodium ions out of the cell and two potassium ions in, both against their concentration gradients. Each cycle of the pump thus removes one positive charge carrier from the intracellular space to maintain the negative resting membrane potential. Because $Na^+/K^+$-ATPase actively pumps sodium and potassium ions against their respective concentration gradients, each cycle of $Na^+/K^+$-ATPase requires energy in the form of adenosine triphosphate (ATP). In neurons, for example, $Na^+/K^+$-ATPase can be responsible for up to ⅔ of the cell's energy expenditure. Without ATP, $Na^+/K^+$-ATPase cannot move the sodium and potassium ions across the membrane, which limits the corresponding neuron's ability to generate an action potential and transmit a signal to the next neuron.

Evidence indicates that the activity of $Na^+/K^+$-ATPase is significantly lower in the brains of patients with neurodegenerative disorders than in the brains of normal controls. One of the most prevalent forms of neurodegenerative diseases is Alzheimer's disease, accounting for approximately 50% to 60% of all dementia cases. Considering that ageing is one of the main risk factors in Alzheimer's disease, and that life expectancy continues to rise in many countries, the prevalence of Alzheimer's disease is likely to increase. At present, no drugs or drug combinations have shown high levels of both safety and efficacy for treating Alzheimer's disease. Accordingly, there is a need for systems and methods for treating Alzheimer's disease and other neurodegenerative diseases.

DETAILED DESCRIPTION

Figure 1:
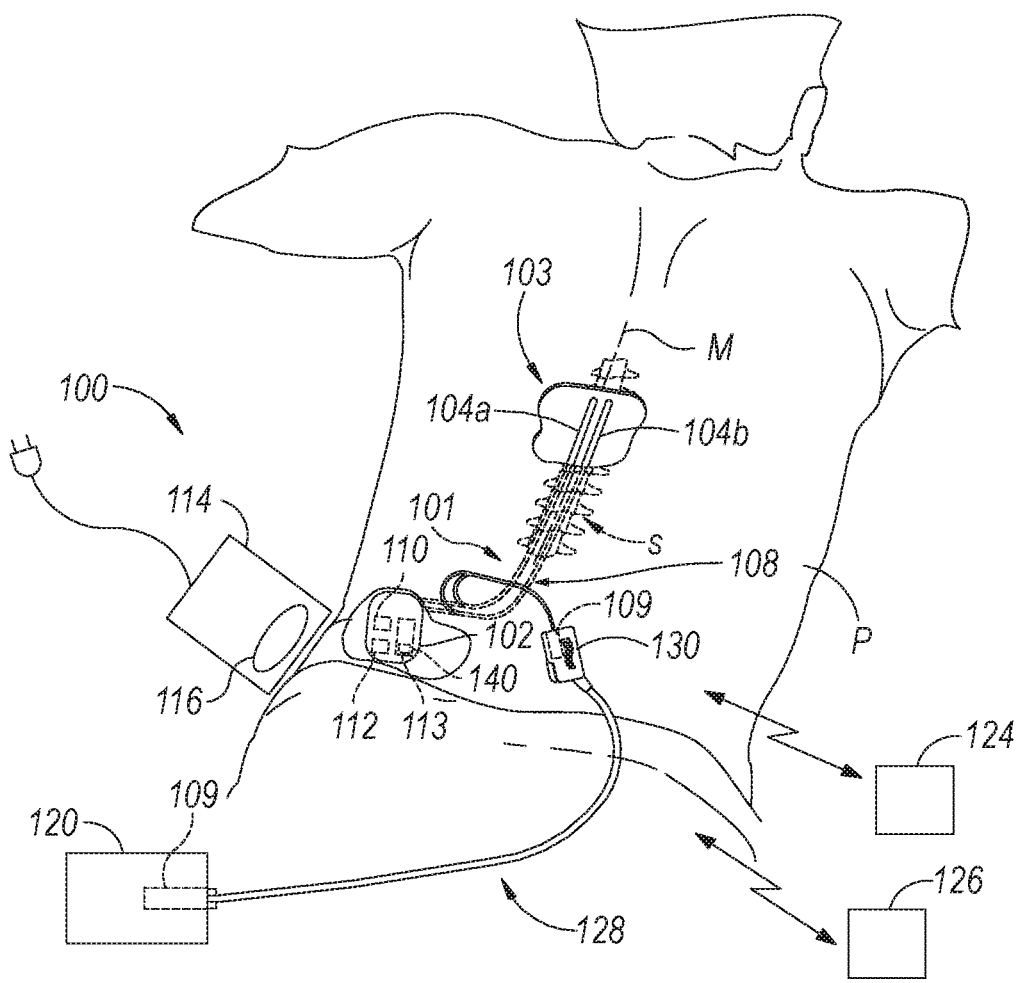
FIG. 1 is a partially schematic illustration of an implantable spinal cord modulation system positioned at the spine to deliver therapeutic signals in accordance with several embodiments of the present technology.

The present technology is directed generally to systems and methods for treating or otherwise addressing one or more neurodegenerative diseases, and in particular, to systems and methods for addressing Alzheimer's disease. As used herein, the term "addressing" a neurodegenerative disease includes treating, curing, slowing the progression of, and/or reducing or eliminating the symptoms of the neurodegenerative disease, unless otherwise specified. Representative therapies in accordance with the present technology can include applying electrical signals to an electrically active tissue, including but not limited to, neural tissue. Such tissue can be located at the spinal cord, the brain, cranial nerves (e.g., the vagal nerve), and/or peripheral nerves. In some embodiments, the present technology includes a treatment system having a signal generator and a signal delivery element configured to apply a high frequency electrical signal to the brain and/or the spinal cord. The high frequency signal is configured to activate $Na^+/K^+$-ATPase neural tissue—without the use of ATP—to restore the signaling capabilities of the neurons. In some embodiments, the signal delivery element is configured to apply a high frequency electrical signal that activates $Na^+/K^+$-ATPase in glial cells (e.g., astrocytes) to restore or improve glial cell uptake of neurotransmitters at neuronal synapses, as described in greater detail below. In some embodiments, prior to application of the electrical signal, one or more lesions of degenerative (e.g., demyelinated) cells can be identified (e.g., via MM) to guide a practitioner positioning the signal delivery element and/or selecting the parameters of treatment (e.g., amplitude, pulse width, frequency, duty cycle, etc.).

Definitions of selected terms are provided under heading 1.0 ("Definitions"). General aspects of the anatomical and physiological environment in which the disclosed technology operates are described below under heading 2.0 ("Introduction"). Particular embodiments of the technology are described under heading 3.0 ("Representative Embodiments") with reference to FIGS. 1-5. Additional embodiments are described under heading 4.0 ("Additional Embodiments).

1.0 Definitions

As used herein, "high frequency" or "HF" refers to a frequency of from about 1.2 kHz to about 100 kHz, or about 1.5 kHz to about 100 kHz, or from about 10 kHz to about 100 kHz, or from about 2 kHz to about 50 kHz, or from about 3 kHz to about 20 kHz, or from about 3 kHz to about 15 kHz, or from about 5 kHz to about 15 kHz, or from about 3 kHz to about 10 kHz, or 1.5 kHz, 2 kHz, 3 kHz, 4 kHz, 5 kHz, 10 kHz, 15 kHz, 20 kHz, 50 kHz, or 100 kHz. The waveform can be biphasic and in some embodiments, symmetrically biphasic. The waveform can have a square shape, a rectangular shape, or other suitable shape. As used herein, the term "about" refers to values within 10% of the stated value. Moreover, as used herein, "low frequency" or "LF" refers to a frequency less than about 1.2 kHz. As used herein, the term "neurodegenerative disease" refers to a disease that results in the progressive loss of structure or function of neurons, including producing the death of neurons. Representative examples of neurodegenerative diseases include Alzheimer's disease and other dementias, Parkinson's disease and related disorders, Prion disease, Motor neurone diseases, Huntington's disease, Spinocerebellar ataxia, Spinal muscular atrophy, Amyotrophic lateral sclerosis, Friedreich's ataxia, and Lewy body disease. As used herein, the term "and/or", as in "A and/or B" refers to A alone, or B alone or A and B.

2.0 Introduction

The human nervous system is comprised of two types of cells: (1) neurons, which generate action potentials and transmit neuronal signals from one part of the body to another, and (2) glia (or glial cells), which provide physical and metabolic support to the neurons. Communication between neurons is achieved by the movement of chemical or electrical signals across a small space (i.e., the synaptic cleft) between adjacent neurons. In the case of chemical communication between neurons, a pre-synaptic (stimulating) neuron releases neurotransmitter molecules that travel across the synaptic cleft and bind to a post-synaptic (stimulated) neuron, thereby linking the action potential of the pre-synaptic neuron with a synaptic potential of the post-synaptic neuron. Once the signal has passed, the neurotransmitter concentration in the synaptic cleft must be reduced to its original level (known as "clearance") in order to prevent over-stimulation of the post-synaptic neuron and/or the potentially toxic build-up of certain neurotransmitters. Neurotransmitter clearance can occur in several ways, one of which is by absorption or uptake by an astrocyte, which is a type of glial cell. In particular, astrocytes are responsible for clearing glutamate—a neurotransmitter highly abundant in the cortex, hippocampus, and caudate nucleus—from synaptic clefts. The ability of astrocytes to efficiently uptake glutamate depends on the ionic and electrochemical gradient of the astrocyte, which is maintained by the astrocyte's $Na^+/K^+$-ATPase.

Recent evidence shows that astrocytes exposed (in vitro) to amyloid beta peptides ("β-amyloid," the molecules that form the toxic plaques that characterize Alzheimer's disease) had (1) reduced $Na^+/K^+$-ATPase activity, and (2) an imbalance of $Na^+$ and $K^+$ ion concentrations. Thus, the impaired functioning of astrocyte $Na^+/K^+$-ATPase may affect astrocyte ability to regulate glutamate concentration and thus contributes to the pathophysiology of Alzheimer's disease and other neurodegenerative diseases by significantly deregulating membrane transport, brain electrophysiological activity, and other important cellular processes. Treatment devices, systems, and methods of the present technology can activate dysfunctional $Na^+/K^+$-ATPase in glial cells (such as astrocytes) via application of a high frequency electrical signal, thereby restoring the signaling capabilities of the surrounding neurons.

3.0 Representative Embodiments

FIG. 1 schematically illustrates a representative treatment system 100 for treating one or more neurodegenerative diseases, such as Alzheimer's disease, arranged relative to the general anatomy of a patient's spinal column. As will be described in further detail later, representative techniques in accordance with the present technology can include treatment applied to the spinal cord, the brain or both. The treatment system 100 can include a signal delivery system 101 having a signal generator 102 (e.g., a pulse generator) and a signal delivery device 103 comprising one or more signal delivery elements 104 (referred to individually as first and second signal delivery elements 104a, 104b, respectively). The signal generator 102 can be connected directly to the signal delivery element 104, or it can be coupled to the signal delivery element 104 via a signal link 108 (e.g., an extension). In some embodiments, the signal generator 102 may be implanted subcutaneously within a patient P. As shown in FIG. 1, the signal delivery element 104 is configured to be positioned at or proximate to the spinal cord and to apply a high frequency electrical signal to the white matter within the spinal cord. Within the nervous system, there are up to 50 times more glial cells than neurons. For example, glial cells comprise 80% of the brain's cells. Moreover, the white matter of the brain and spinal cord have an especially high proportion of glial cells to neurons. Thus, it is believed that delivering high frequency modulation at or proximate the white matter can activate $Na^+/K^+$-ATPase in nearby glial cells, such as astrocytes.

In a representative embodiment, the signal delivery device 103 includes first and second signal delivery elements 104a, 104b, each of which comprises a flexible, isodiametric lead or lead body that carries features or structures for delivering an electrical signal to the treatment site after implantation. As used herein, the terms "lead" and "lead body" include any of a number of suitable substrates and/or support members that carry structures for providing therapy signals to the patient. For example, the lead body can include one or more electrodes or electrical contacts that direct electrical signals into the patient's tissue, such as to activate $Na^+/K^+$-ATPase without the presence of ATP. Accordingly if the patent's disease state blocks a pathway to generate ATP, the electrical signal can replace the function of ATP to activate an ion pump. In other embodiments, the signal delivery device 103 and/or signal delivery elements 104 can include devices other than a lead body (e.g., a paddle) that also direct electrical signals and/or other types of signals to the patient. Additionally, although FIG. 1 shows an embodiment utilizing two signal delivery elements 104, in other embodiments the signal delivery system 101 and/or signal delivery device 103 can include more or fewer signal delivery elements (e.g., one signal delivery element 104, three signal delivery elements 104, four signal delivery elements 104, etc.), each configured to apply electrical signals at different locations and/or coordinate signal delivery to deliver a combined signal to the same (or generally the same) anatomical location.

As shown in FIG. 1, the first signal delivery element 104a may be implanted on one side of the spinal cord midline M, and the second signal delivery element 104b may be implanted on the other side of the spinal cord midline M. For example, the first and second signal delivery elements 104a, 104b shown in FIG. 1 may be positioned just off the spinal cord midline M (e.g., about 1 mm offset) in opposing lateral directions so that first and second signal delivery elements 104a, 104b are spaced apart from each other by about 2 mm. In some embodiments, the signal delivery devices 104a, 104b can be placed directly side by side with no separation. In some embodiments, the first and second signal delivery elements 104a, 104b may be implanted at a vertebral level ranging from, for example, about T8 to about T12. In other embodiments, one or more signal delivery devices can be implanted at other vertebral levels, e.g., as disclosed in U.S. Pat. No. 9,278,215, filed Sep. 7, 2012, which is incorporated herein by reference in its entirety. In general, the vertebral location may grossly, approximately or generally match the primary spinal segment that processes afferent information for the body segment that has a compromised function resulting from neurodegeneration. For example, for a spinal cord lesion existing at the L5-S1 spinal segment, sensation and function of the foot may be compromised (as the L5-S1 dermatomes overlay the feet). The level to start applying the electrical therapy may accordingly be at or near the T11-T12 vertebral region. It is emphasized that this may be only a starting point, as disease processes are known to alter neural representation, especially in cases where neurodegeneration has occurred or is occurring. Additionally, diseases affecting visceral organs have a less specific mapping to the spinal cord, and so specific vertebral targets for visceral dysfunction might be more diffuse.

The signal generator 102 can transmit signals (e.g., electrical therapy signals or other therapy signals) to the signal delivery element 104 that up-regulate (e.g., stimulate or excite) and/or down-regulate (e.g., block or suppress) target nerves (e.g., local vagal nerves). As used herein, and unless otherwise noted, to "modulate," "stimulate," or provide "modulation" or "stimulation" to the target nerves refers generally to having either type of the foregoing effects on the target nerves. The signal generator 102 can include a machine-readable (e.g., computer-readable) medium containing instructions for generating and transmitting suitable therapy signals. The signal generator 102 and/or other elements of the treatment system 100 can include one or more processors 110, memories 112 and/or input/output devices 140. Accordingly, the process of providing electrical signals, detecting physiological parameters of the patient, adjusting the modulation signal, and/or executing other associated functions can be performed by computer-executable instructions contained by computer-readable media located at the signal generator 102 and/or other system components. The signal generator 102 can include multiple portions, elements, and/or subsystems (e.g., for directing signals in accordance with multiple signal delivery parameters) housed in a single housing, as shown in FIG. 1, or in multiple housings.

The signal delivery system 101 can include one or more sensing elements 113 for detecting one or more physiological parameters of the patient before, during, and/or after the application of electrical therapy signals. In some embodiments, one or more of the sensing elements 113 can be carried by the signal generator 102, the signal delivery element, and/or other implanted components of the system 101. In other embodiments, the sensing element(s) 113 can be an extracorporeal or implantable device separate from the signal generator 102 and/or signal delivery element 104. Representative sensing elements 113 include one or more of: a subcutaneous sensor, a temperature sensor, an impedance sensor, a chemical sensor, a biosensor, an electrochemical sensor, a hemodynamic sensor, an optical sensor and/or other suitable sensing devices. Representative physiological parameters detected by the sensing element(s) 113 can include neurotransmitter concentration, local impedance, current, and/or voltage levels, and/or any correlates and/or derivatives of the foregoing parameters (e.g., raw data values, including voltages and/or other directly measured values).

The signal generator 102 can also receive and respond to an input signal received from one or more sources. The input signals can direct or influence the manner in which the therapy and/or process instructions are selected, executed, updated, and/or otherwise performed. The input signals can be received from one or more sensors 113 that are carried by the signal generator 102 and/or distributed outside the signal generator 102 (e.g., at other patient locations) while still communicating with the signal generator 102. The sensors 113 and/or other input devices 140 can provide inputs that depend on or reflect patient state (e.g., patient position, patient posture, and/or patient activity level), and/or inputs that are patient-independent (e.g., time). Still further details are included in U.S. Pat. No. 8,355,797, filed Feb. 10, 2010, which is incorporated herein by reference in its entirety.

In some embodiments, the signal generator 102 can obtain power to generate the therapy signals from an external power source 114. The external power source 114 can transmit power to the implanted signal generator 102 using electromagnetic induction (e.g., RF signals). For example, the external power source 114 can include an external coil 116 that communicates with a corresponding internal coil (not shown) within the implantable signal generator 102. The external power source 114 can be portable for ease of use.

In another embodiment, the signal generator 102 can obtain the power to generate therapy signals from an internal power source, in addition to or in lieu of the external power source 114. For example, the implanted signal generator 102 can include a non-rechargeable battery or a rechargeable battery to provide such power. When the internal power source includes a rechargeable battery, the external power source 114 can be used to recharge the battery. The external power source 114 can in turn be recharged from a suitable power source (e.g., conventional wall power).

During at least some procedures, an external generator 120 (e.g., a trial stimulator or modulator) can be coupled to the signal delivery element 104 during an initial procedure, prior to implanting the signal generator 102. For example, a practitioner (e.g., a physician and/or a company representative) can use the external generator 120 to generate the therapy signal and vary the modulation parameters provided to the signal delivery elements 104 in real time, and select optimal or particularly efficacious parameters. These parameters can include the location from which the electrical signals are emitted, as well as the characteristics of the electrical signals provided to the signal delivery elements 104. In some embodiments, input is collected via the external generator and can be used by the clinician to help determine what parameters to vary. In a typical process, the practitioner uses a cable assembly 128 to temporarily connect the external generator 120 to the signal delivery element 104. The practitioner can test the efficacy of the signal delivery elements 104 in an initial position. The practitioner can then disconnect the cable assembly 128 (e.g., at a connector 130), reposition the signal delivery elements 104, and reapply the electrical signal. This process can be performed iteratively until the practitioner obtains the desired signal parameters and/or position for the signal delivery element 104. Optionally, the practitioner can move the partially implanted signal delivery element 104 without disconnecting the cable assembly 128. Furthermore, in some embodiments, the iterative process of repositioning the signal delivery devices 110 and/or varying the therapy parameters may not be performed. Instead, the practitioner can place the signal delivery element(s) 104 at an appropriate anatomical location, and then select which electrodes or contacts deliver the therapy signal, as a way of varying the location to which the therapy signal is directed, without repositioning the signal delivery element(s) 104.

After the signal delivery elements 104 are implanted, the patient P can receive therapy via signals generated by the external generator 120, typically for a limited period of time. During this time, the patient wears the cable assembly 128 and the external programmer outside the body. Assuming the trial therapy is effective or shows the promise of being effective, the practitioner then replaces the external generator 120 with the implanted signal generator 102, and programs the signal generator 102 with therapy programs selected based on the experience gained during the trial period. Optionally, the practitioner can also replace the signal delivery elements 104. The signal delivery parameters provided by the signal generator 102 can still be updated after the signal generator 102 is implanted, via a wireless physician's programmer 124 (e.g., a physician's remote) and/or a wireless patient programmer 126 (e.g., a patient remote). Generally, the patient P has control over fewer parameters than does the practitioner. For example, the capability of the patient programmer 126 may be limited to starting and/or stopping the signal generator 102, and/or adjusting the signal amplitude. The patient programmer 126 may be configured to accept pain relief input as well as other variables, such as medication use.

The signal generator 102, the lead extension, the external generator 120 and/or the connector 130 can each include a receiving element 109. Accordingly, the receiving elements 109 can be patient implantable elements, or the receiving elements 109 can be integral with an external patient treatment element, device or component (e.g., the external generator 120 and/or the connector 130). The receiving elements 109 can be configured to facilitate a simple coupling and decoupling procedure between the signal delivery elements 104, the lead extension, the pulse generator 101, the external generator 120 and/or the connector 130. The receiving elements 109 can be at least generally similar in structure and function to those described in U.S. Patent Application Publication No. 2011/0071593, incorporated by reference herein in its entirety.

In any of the foregoing embodiments, the parameters in accordance with which the signal generator 102 provides signals can be adjusted during portions of the therapy regimen. For example, the frequency, amplitude, pulse width, and/or signal delivery location can be adjusted in accordance with a pre-set therapy program, patient and/or physician inputs, and/or in a random or pseudorandom manner. Such parameter variations can be used to address a number of potential clinical situations. Certain aspects of the foregoing systems and methods may be simplified or eliminated in particular embodiments of the present disclosure. Further aspects of these and other expected beneficial results are detailed in U.S. Patent Application Publication Nos. 2010/0274317, 2009/0204173, 2010/0191307, 2010/0274312, 2010/0274314, 2012/0172946, and U.S. Pat. Nos. 8,712,533 and 9,327,121, each of which is incorporated herein by reference in its entirety.

Figure 2:
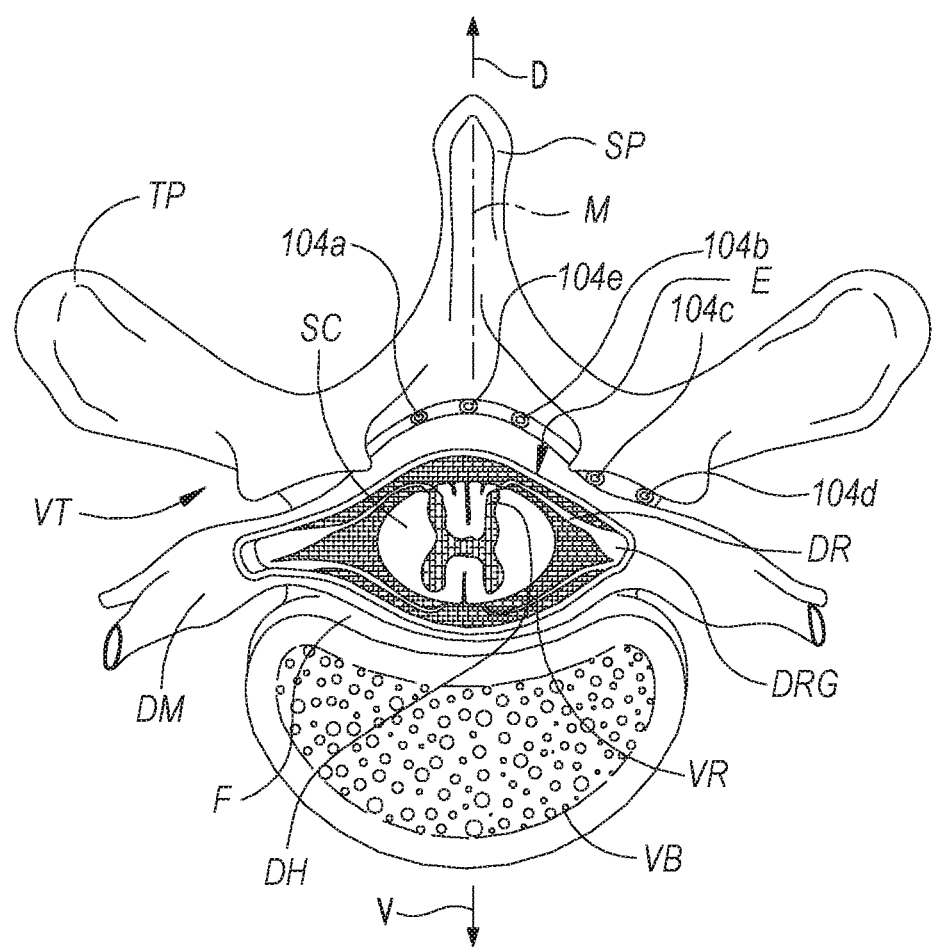
FIGS. 2 and 3 are partially schematic, cross-sectional illustrations of a patient's spine, illustrating representative locations for implanted lead bodies in accordance with embodiments of the present technology.
Figure 3:
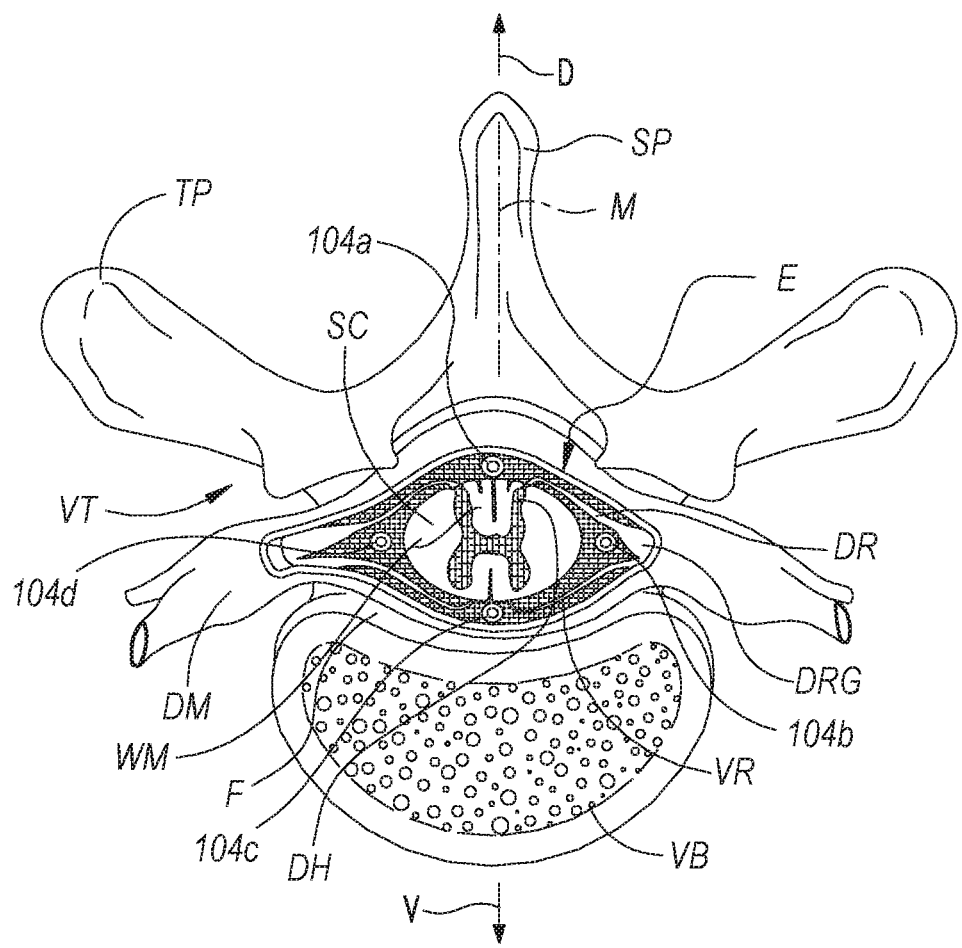

FIG. 2 is a cross-sectional illustration of a spinal cord SC and an adjacent vertebra VT (based generally on information from Crossman and Neary, "Neuroanatomy," 1995 (published by Churchill Livingstone)), along with multiple signal delivery elements 104 (shown as signal delivery elements 104a-104e) implanted at representative locations. For purposes of illustration, multiple signal delivery elements 104 are shown in FIG. 2 implanted in a single patient. In actual use, any given patient will likely receive fewer than all the signal delivery elements 104 shown in FIG. 2.

As shown in FIG. 2, the spinal cord SC is situated within a vertebral foramen F, between a ventrally located ventral body VB and a dorsally located transverse process TP and spinous process SP. Arrows V and D identify the ventral and dorsal directions, respectively. The spinal cord SC itself is located within the dura mater DM, which also surrounds portions of the nerves exiting the spinal cord SC, including the ventral roots VR, dorsal roots DR and dorsal root ganglia DRG. The dorsal roots DR enter the spinal cord SC at the dorsal root entry zone E, and communicate with dorsal horn neurons located at the dorsal horn DH. In one embodiment, the first and second signal delivery elements 104a, 104b are positioned just off the spinal cord midline M (e.g., about 1 mm. offset) in opposing lateral directions so that the two signal delivery elements 104a, 104b are spaced apart from each other by about 2 mm. In other embodiments, a lead or pairs of leads can be positioned at other epidural locations, e.g., toward the outer edge of the dorsal root entry zone E as shown by a third signal delivery element 104c, or at the dorsal root ganglia DRG, as shown by a fourth signal delivery element 104d, or approximately at the spinal cord midline M, as shown by a fifth signal delivery element 104e.

In some embodiments, it may be advantageous to position one or more signal delivery elements 104 within the dura mater DM to better target one or more glial cells present in the white matter of the spinal cord SC. For example, as shown in the cross-sectional view of a spinal cord SC in FIG. 3, in some embodiments a first signal delivery element 104a and a second signal delivery element 104c are positioned along the spinal cord midline M on the dorsal and ventral sides of the spinal cord SC, respectively. In other embodiments, one or more signal delivery elements 104 can be positioned at other locations. For example, in some embodiments a third signal delivery element 104b and a fourth signal delivery element 104d are positioned off the spinal cord midline M on opposing lateral sides of the spinal cord SC. In other embodiments, one or more signal delivery elements 104 may be positioned in other suitable locations within the subdural space. Additionally, in a particular embodiment, a physician may position one or more signal delivery elements in the epidural space and/or one or more signal delivery elements in the subdural space. Positioning one or more signal delivery elements in the subdural space may be advantageous, for example, because of the closer proximity to the white matter WM.

Figure 4:
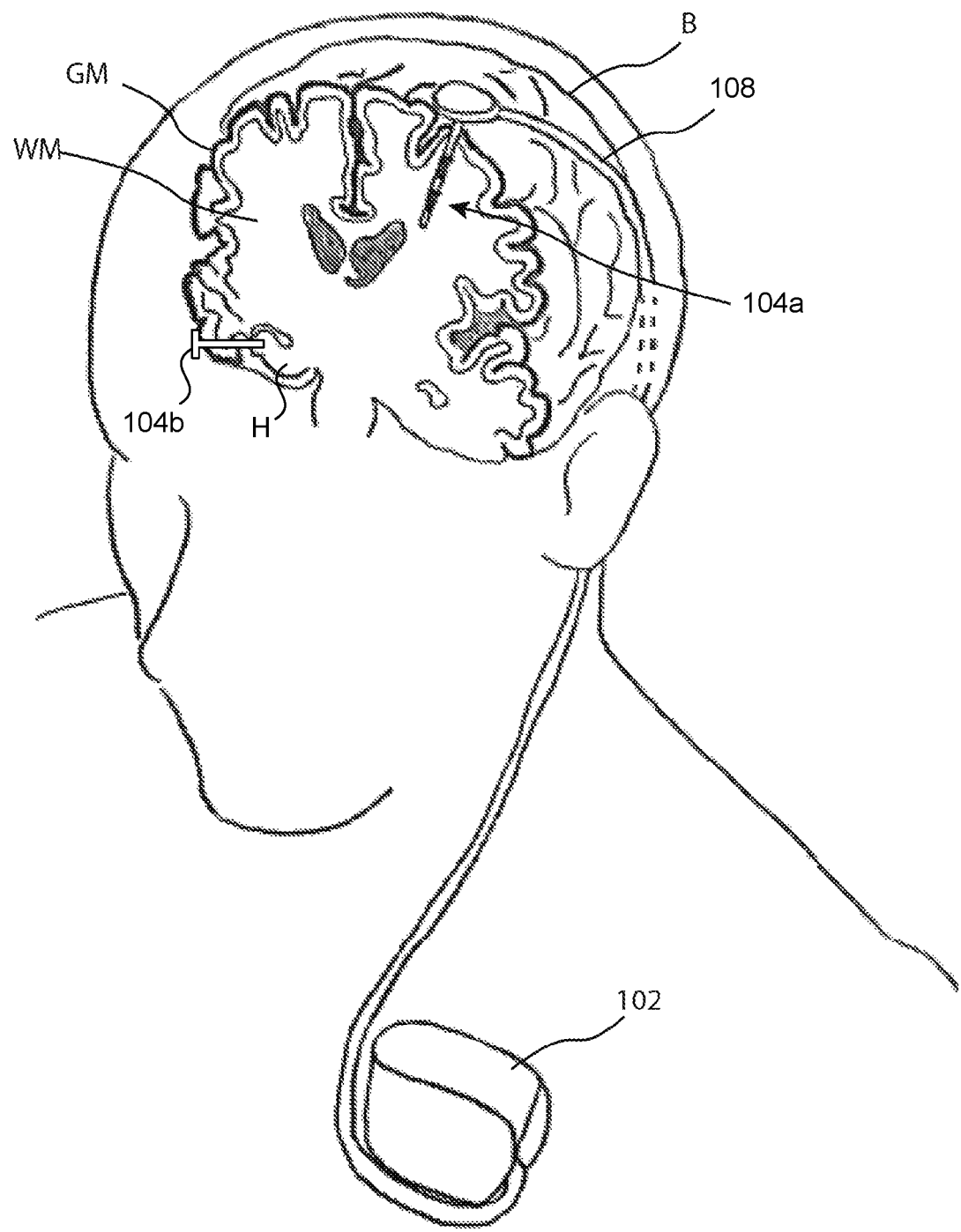
FIG. 4 is a partially schematic, cross-sectional illustration of a patient's brain, illustrating representative locations for implanted lead bodies for deep brain stimulation in accordance with embodiments of the present technology.

In some aspects of the present technology, one or more signal delivery elements 104 may be positioned within the patient's head, to deliver a therapy signal to a lobe or portion of the deep brain or cortex. For example, FIG. 4 shows a patient's brain B, including the gray matter GM and white matter WM, with a first signal delivery element 104a positioned at or within the white matter WM of the deep brain region. As used herein, the terms "at or within," "proximate," "at or proximate," "at or near," etc. refer to a position close enough to the target area to have a therapeutic effect (e.g., within 1 mm of the target nervous tissue, within 5 mm of the target nervous tissue, etc.). Examples of deep brain regions that can be stimulated include, for example, the anterior thalamus, the ventrolateral thalamus (Thal), the internal segment of globus pallidus (GPi), the substantia nigra pars *reticulata* (SNr), the subthalamic nucleus (STN), the external segment of globus pallidus (GPe), the neostriatum, cingulate, the cingulate gyms, pedunculopontine nucleus, and/or others For example, as shown in FIG. 4, in some embodiments it may be advantageous to position a second signal delivery element 104b at the hippocampus H, as the hippocampus and cortex show the highest concentrations of brain glutamate and, as described above, the impaired functioning of astrocyte $Na^+/K^+$-ATPase affects the $Na^+$ gradient, thereby affecting astrocyte ability to regulate glutamate concentration and contributing to the pathophysiology of Alzheimer's disease. In addition, recent studies show that hippocampal neurons in mice have increased excitability in response to high frequency stimulation. Thus, high frequency stimulation at the hippocampus and/or cortex can activate the dysfunctional $Na^+/K^+$-ATPase of astrocytes at or within the hippocampal tissue to maintain the $Na^+$ gradient, thereby providing the energy necessary for glutamate uptake without the presence of ATP. As described above, this can be advantageous when the normal ATP generation channels are blocked or otherwise ineffective.

Examples of veins providing access to the deep brain include the inferior sagittal sinus, pericallosal sinus, cavernous sinus, sphenoid sinus, temporal basal vein, and occipital veins. Examples of arteries providing access to the deep brain include any branches off the internal carotid or vertebral arteries. Examples of veins providing access to the sphenopalatine ganglion (SPG) include the superficial temporal veins and the facial vein. Examples of arteries providing access to the SPG include the maxillary artery, descending palatine artery, and facial artery.

Figure 5:
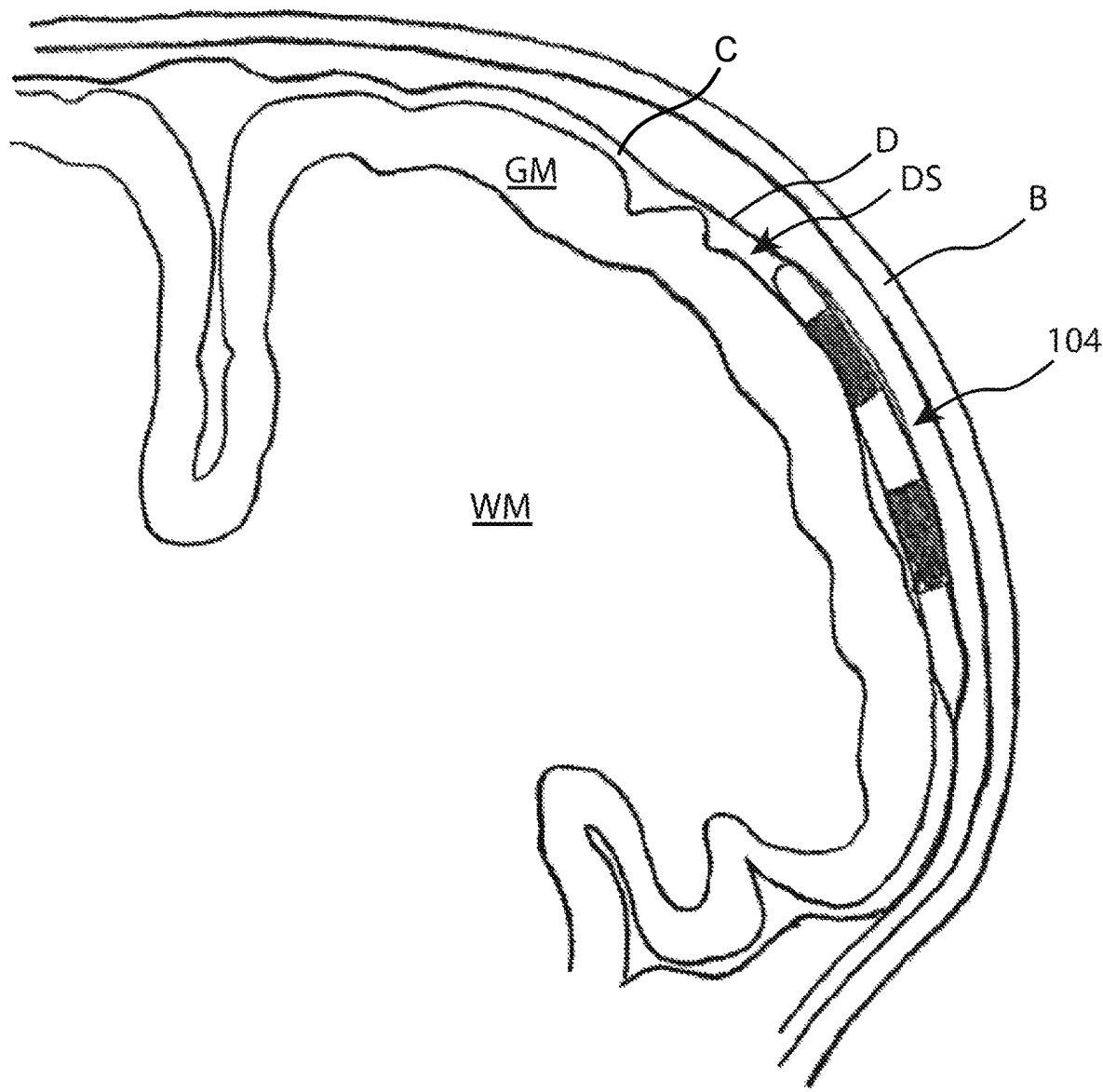
FIG. 5 is a partially schematic, cross-sectional illustration of a patient's brain, illustrating representative locations for implanted lead bodies in accordance with embodiments of the present technology.

FIG. 5 shows a signal delivery element 104 positioned within a subdural space DS in contact with the cortex C of the brain. In some embodiments, cortical stimulation will be less invasive than deep brain stimulation. Conversely, deep brain stimulation can provide access to neural targets that are not accessible via cortical stimulation. Examples of cortical regions of the brain that may be stimulated include the motor strip, the sensory strip, the pre-motor cortex, and other suitable regions. The signal delivery element(s) 104 can be delivered to any of a number of vessels in order to place the electrodes adjacent the cortical tissue to be stimulated. For cortical stimulation or any stimulation detailed herein, it may be particularly advantageous to utilize a signal delivery element (not shown) formed of concentric outer and inner ring electrodes (e.g., in the form of a "bulls-eye" target. In such an embodiment, the signal delivery element can be positioned at the treatment site such that the neural tissue is positioned between the outer and inner electrodes. When the signal is delivered to the electrodes, an electric current flows between the inner and outer electrodes, thereby targeting neurons or glial cells positioned therebetween.

Examples of veins providing access to the cortex include the superior sagittal sinus, any of the superior cerebral veins branching from the superior sagittal sinus (e.g., the lacuna, the frontopolar vein, the anterior frontal vein, the posterior frontal vein, the precentral vein, the central vein, the anterior parietal vein, the posterior parietal vein, and the occipital vein), the superior sylvian vein, the vein of Labbe, the vein of Trolard, the inferior sagittal sinus, and any suitable inferior cerebral veins branching off of the inferior sagittal sinus, transverse sinus, and meningeal sinus. Examples of arteries providing access to the cortex include any of the branches off of the external carotid arteries, the maxillary arteries, or the meningeal arteries.

In some embodiments, the signal delivery element(s) 104 can be intravascularly introduced within the patient's head adjacent a selected brain region, or the signal delivery element can be non-vascularly introduced within the patient's head, e.g., through a burr hole drilled in the patient's cranium, or by performing a craniotomy. In those embodiments for which the signal delivery elements are introduced intravascularly, the jugular and femoral veins can be used as intravascular access points from which the signal delivery element(s) can be delivered to the above-described veins, and the carotid or femoral arteries can be used as intravascular access points from which the signal delivery element(s) can be delivered to the above-described arteries. In those brain regions that are not adjacent easily-accessible or navigable blood vessels, access to the treatment site may be achieved by non-vascular techniques, e.g., by penetrating the parenchyma for deep brain stimulation (as shown in FIG. 4), or by epidurally or subdurally placing the signal delivery element(s) 104 along the cortex for cortical simulation (as shown in FIG. 5). Thus, it can be appreciated that a combination of intravascular and non-vascular placement of the signal delivery element(s) 104 can be utilized in procedures involving multiple brain regions.

After the leads have been deployed within the spinal cord and/or the brain, a high frequency signal can be applied to activate the $Na^+/K^+$-ATPase of the targeted neurons and/or deactivate one or more glial cells. For example, the result of "replacing" the ATP with electrical energy can be to allow the neurons to function appropriately. If that result improves the disease state, the systemic neuroimmune response will abate, and the glia will be less activated from external drivers. In addition to or in lieu of the foregoing effect, if the glial dysfunction is tied to chronic ATP starving, the glia may functionally normalize as a result of the electrical therapy signal.

In particular embodiments, representative current amplitudes for the therapy signal are from 0.1 mA to 20 mA, or 0.5 mA to 10 mA, or 0.5 mA to 7 mA, or 0.5 mA to 5 mA.

Representative pulse widths range from about 10 µs to about 333 µs, about 10 µs to about 166 µs, about 10 µs to about 30 µs, about 20 µs to about 100 µs, about 30 µs to about 100 µs, and about 30 µs to about 40 µs. Duty cycles can range from about 10% to about 100%, and in a particular duty cycle, signals are delivered for 20 seconds and interrupted for 2 minutes (an approximately 14% duty cycle). For example, for a 10 kHz signal, the duty cycle can be 10%. In other embodiments, these parameters can have other suitable values. For example, in at least some embodiments, the foregoing systems and methods may be applied to therapies that have frequencies outside the ranges discussed above (e.g., 1.5 kHz-100 kHz) but which also do not produce paresthesia. The absence of paresthesia (which may result from lower frequency stimulation to targets other than deep brain targets), is typically preferred by patients, and can reduce the clinical burden on practitioners. Representative pulse widths (which can be delivered at frequencies above or below 1.5 kHz, depending upon the embodiment) include pulse widths from 10-50 µs, 20-40 µs, 25-35 µs, 30-35 µs, and 30 µs. The ranges for individual parameters may be combined in a variety of suitable manners, depending on factors including patient indication. In some embodiments, a high frequency sign (above 1.2 kHz or above 1.5 kHz) can be provided in combination with a low frequency signal (e.g., below 1.2 kHz) to provide the patient with benefits that may be unique to each.

Initial in vitro studies conducted by the present Applicant indicated that high frequency signals at or above 50 kHz with a duty cycle of at least 0.001% (of a one second period) may be particularly effective at hyperpolarizing neurons and consequently activating $Na^+/K^+$-ATPase. For example, in one embodiment, the high frequency signal can have a frequency of at least 50 kHz, a pulse width of at least 10 µs, and a duty cycle of at least 0.001% (based on a one second period). In another embodiment, the high frequency signal can be a biphasic waveform with a frequency of at least 100 kHz, a pulse width of at least 5 µs. In a particular embodiment, the high frequency signal can have a frequency of at least 10 kHz and a duty cycle of at least 10%. In some embodiments, for signal frequencies between 10 kHz and 50 kHz, the corresponding pulse width and duty cycle values can be interpolated from the above-mentioned pulse width and duty cycle values at 10 kHz and 50 kHz.

In some embodiments, prior to application of the electrical signal, one or more lesions of degenerative (e.g., demyelinated) cells can be identified (e.g., via MRI) to guide positioning of the signal delivery element and/or the parameters of treatment (e.g., amplitude, pulse width, frequency, duty cycle, etc.).

The treatment systems disclosed herein can include other features in addition to or in lieu of features described above. For example, one feature of at least some of the foregoing embodiments is that the charging parameters for the battery of an implantable pulse generator can be tailored, adjusted, determined, calculated, set, or otherwise established in a manner that reflects patient-specific and/or battery-specific characteristics. An advantage of this arrangement is that it can extend the life of the battery and thereby reduce or even eliminate the need to replace the battery.

Another feature of at least some of the foregoing embodiments is that the processes for establishing and/or adjusting the charge and/or discharge parameters can be automated. An advantage of this feature is that it can reduce or eliminate any effort on the part of the patient and/or the practitioner and/or the company representative to achieve the benefits of tailored charge/discharge parameters. Still another advantage of the foregoing features is that, in particular embodiments, the patients perception of the consistency of the system can be improved. For example, by automatically providing and adjusting (as needed) the margins within which the IPG battery operates, the patient will be less likely to over-discharge the battery.

From the foregoing, it will be appreciated that specific embodiments of the disclosed technology have been described herein for purposes of illustration, but that various modifications to or combinations of the disclosed embodiments may be made without deviating from the technology. For example, in some embodiments one or more areas (e.g., deep brain and cortical brain, spinal cord and deep brain, spinal cord and cortical brain, spinal cord, deep brain, and cortical brain, etc.) may be treated simultaneously or alternatingly to achieve a synergistic effect. For example, the brain typically receives more abstract information regarding somatosensory inputs than the spinal cord. High frequency stimulation at the brain can modulate the more abstract information, while high frequency stimulation at the spinal cord can modulate the more particularized, less abstract information. Thus, the combination of brain and spinal cord stimulation can benefit from exclusive access to certain differential processing by information type.

Although the treatment systems of the present technology have been described with reference to treating or slowing the progression of Alzheimer's disease, other neurodegenerative diseases may also be addressed by the present technology, such as multiple sclerosis, Parkinson's disease, and epilepsy. Certain aspects of the technology described in the context of particular embodiments may be combined or eliminated in other embodiments. Further, while advantages associated with certain embodiments of the disclosed technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

To the extent any materials incorporated herein by reference conflict with the present disclosure, the present disclosure controls.

We claim:

1. A method for treating a patient, comprising:
   addressing a neurodegenerative disease in the patient by applying an electrical signal to the patient via a treatment system that includes a signal delivery element positioned at or within white matter of the patient's brain, the electrical signal having a frequency of from about 5 kHz to about 100 kHz.

2. The method of claim 1 wherein applying the electrical signal includes applying the electrical signal to one or more glial cells present in the white matter at or proximate the signal delivery element.

3. The method of claim 2 wherein applying the electrical signal to the one or more glial cells includes applying the electrical signal to one or more astrocytes in the white matter at or proximate the signal delivery element.

4. The method of claim 1 wherein the electrical signal has a frequency of at least 50 kHz.

5. The method of claim 1 wherein applying the electrical signal includes modulating ion-pump activity of one or more neurons and/or glial cells within the white matter of the brain without the use of ATP.

6. The method of claim 1 wherein applying the electrical signal includes applying the electrical signal to a signal delivery element positioned at the hippocampus.

7. The method of claim 1 wherein applying the electrical signal includes applying the electrical signal having a pulse width of from about 10 µs to about 30 µs.

8. A method for treating a neurodegenerative disease of a patient, comprising:
   in response to an indication of a degenerative lesion within white matter of the patient's brain, applying an electrical signal to the patient via a treatment system that includes a signal delivery element positioned at or proximate the lesion and in electrical communication with the lesion, the electrical signal having a frequency of from about 5 kHz to about 100 kHz.

9. The method of claim 8 wherein applying the electrical signal includes applying the electrical signal to one or more astrocytes in the white matter at or proximate the signal delivery element.

10. The method of claim 8 wherein the electrical signal has a frequency of at least 50 kHz.

11. The method of claim 8 wherein applying the electrical signal includes modulating ion-pump activity of one or more neurons and/or glial cells within the white matter of the brain.

12. The method of claim 11 wherein applying the electrical signal includes activating one or more ion-pumps of the one or more neurons and/or glial cells via application of the electrical signal and without the use of ATP.

13. The method of claim 8 wherein applying the electrical signal includes applying the electrical signal having a pulse width of from about 10 µs to about 30 µs.

14. A method for treating a patient, comprising:
   addressing a neurodegenerative disease in the patient by applying an electrical signal to the patient via a treatment system that includes a signal delivery element positioned at or within white matter of the patient's brain, wherein the electrical signal is applied to one or more astrocytes present in the white matter at or proximate the signal delivery element, the electrical signal having a frequency of at least 50 kHz,
   wherein applying the electrical signal includes modulating ion-pump activity of one or more neurons and/or glial cells within the white matter of the brain without the use of ATP.

* * * * *

UNITED STATES PATENT AND TRADEMARK OFFICE
CERTIFICATE OF CORRECTION

PATENT NO. : 11,123,565 B1  
APPLICATION NO. : 15/798110  
DATED : September 21, 2021  
INVENTOR(S) : Thacker et al.

Page 1 of 1

It is certified that error appears in the above-identified patent and that said Letters Patent is hereby corrected as shown below:

On the Title Page

Item (74), in Column 2, in "Attorney, Agent, or Firm", Line 1, delete "Perkin" and insert -- Perkins Coie LLP --, therefor.

In the Specification

In Column 3, Line 14, delete "MM)" and insert -- MRI) --, therefor.

In Column 8, Line 52, delete "mm." and insert -- mm --, therefor.

In Column 9, Line 35, delete "others" and insert -- others. --, therefor.

Signed and Sealed this  
Eighth Day of March, 2022

Drew Hirshfeld  
*Performing the Functions and Duties of the  
Under Secretary of Commerce for Intellectual Property and  
Director of the United States Patent and Trademark Office*